(12) United States Patent
Van Nijnatten

(10) Patent No.: US 11,266,359 B2
(45) Date of Patent: Mar. 8, 2022

(54) DEVICE AND METHOD FOR DETERMINING A VOLUME OF PROJECTION OF A DUAL-AXIS COMPUTED TOMOGRAPHY SYSTEM

(71) Applicant: KONINKLIJKE PHILIPS N.V., Eindhoven (NL)

(72) Inventor: Fred Simon Berend Van Nijnatten, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 100 days.

(21) Appl. No.: 16/650,066

(22) PCT Filed: Sep. 18, 2018

(86) PCT No.: PCT/EP2018/075131
§ 371 (c)(1),
(2) Date: Mar. 24, 2020

(87) PCT Pub. No.: WO2019/063345
PCT Pub. Date: Apr. 4, 2019

(65) Prior Publication Data
US 2020/0289065 A1   Sep. 17, 2020

(30) Foreign Application Priority Data
Sep. 26, 2017 (EP) .................... 17193169

(51) Int. Cl.
*A61B 6/00* (2006.01)
*A61B 6/03* (2006.01)

(52) U.S. Cl.
CPC ............ *A61B 6/032* (2013.01); *A61B 6/4441* (2013.01); *A61B 6/4458* (2013.01); *A61B 6/542* (2013.01); *A61B 6/58* (2013.01)

(58) Field of Classification Search
CPC ........... A61B 6/027; A61B 6/032; A61B 6/06; A61B 6/4441; A61B 6/4458; A61B 6/469;
(Continued)

(56) References Cited

U.S. PATENT DOCUMENTS 8,745,789 B2 * 6/2014 Saracen ............... A61N 5/1049
5/601
2009/0262886 A1 10/2009 Mollus et al.
(Continued)

FOREIGN PATENT DOCUMENTS

WO 2008015611 A2 2/2008

OTHER PUBLICATIONS

PCT/EP2018/075131, ISR & WO, dated Nov. 28, 2018, 16 Page Document.
(Continued)

*Primary Examiner* — Irakli Kiknadze

(57) ABSTRACT

The present invention relates to a device for determining a volume of projection of a dual-axis computed tomography system with at least one shutter, the device (1) comprising: an interface unit (2); a projection module (3); and a position determination module (4); wherein the interface unit (2) is configured to receive a volume of interest (44) for a computed tomography image showing an object (22); wherein the projection module (3) is configured to determine a volume of projection (41, 42, 46) of a detector (16) based on different simulated positions of the detector (16) on a trajectory around the object (22) and based on a variable simulated position of at least one shutter (15); and wherein the position determination module (4) is configured to determine the simulated position of the at least one shutter (15) for each determined simulated position of the detector (16) such that the volume of projection (41, 42, 46) corre-
(Continued)

sponds to the volume of interest (44). The present invention avoids that parts of an object of interest are unintentionally not imaged in dual-axis computed tomography imaging whilst reducing x-ray absorption to parts of the object outside the volume of interest (44) and provides improved insight in the volume of projection (41, 42, 46) of a dual-axis trajectory acquisition.

20 Claims, 4 Drawing Sheets

(58) Field of Classification Search
CPC .. A61B 6/542; A61B 6/58; A61B 6/00; A61B 6/037; A61B 6/4275; A61B 6/4417; A61B 6/4476; A61B 6/466; A61B 6/5235; A61B 6/4035; A61B 6/42; A61B 6/4233; A61B 6/5205; A61B 6/582; A61B 6/583; A61B 6/584; A61B 6/03; A61B 6/4266; A61B 6/488; A61B 5/0062; A61B 5/0066; A61B 5/0068; A61B 5/0073; A61B 5/0075; A61B 5/0084; A61B 5/6852; A61B 17/435; A61B 6/035; A61B 6/4085; A61B 2017/00699; A61B 2034/2061; A61B 2562/0266; A61B 5/055; A61B 5/1077; A61B 5/113; A61B 5/6801; G21K 1/04; G21K 1/043; G21K 1/025; G21K 1/046; G21K 2201/067; G01N 23/046; G01N 2021/1765; G01N 21/25; G01N 21/27; G01N 21/4795; G01N 21/6458; G01N 21/6486; G01N 2223/419; G01N 33/4833; G01N 21/453; G06T 11/005; G06T 2211/412; A61N 2005/1054; A61N 2005/1061; A61N 2005/1074; A61N 2005/1095; A61N 5/1042; A61N 5/1049; A61N 5/1067; A61N 5/108; A61N 2005/1059; A61N 2005/1089; A61N 5/1037; A61N 5/1082; G01T 1/1614; G01T 1/1615; G01T 1/1642; G01T 1/1648; G01T 1/2985; G01T 11/005; G01T 2211/412; H05H 15/00; G01B 9/02; G01B 9/02027; G01B 9/02049; G01B 9/02064; G01B 9/02087; G01B 9/02091; G01B 9/40; A61G 11/00
USPC ................................. 378/4, 19, 62
See application file for complete search history.

(56) References Cited

U.S. PATENT DOCUMENTS

| | | |
|---|---|---|
| 2010/0014740 A1 | 1/2010 | Movassaghi et al. |
| 2011/0182492 A1 | 7/2011 | Grass et al. |
| 2013/0343631 A1 | 12/2013 | Florent et al. |
| 2015/0103972 A1* | 4/2015 | Bredno ............... A61B 6/4233 378/7 |
| 2015/0305703 A1 | 10/2015 | Kim et al. |
| 2018/0304098 A1* | 10/2018 | Humber ............... A61B 6/4085 |

OTHER PUBLICATIONS

Wang et al.: "A Cone-Beam Reconstruction Algorithm for Circle-Plus-Arc Data-Acquisition Geometry"; IEEE Transactions on Medical Imaging, vol. 18, NPO. 9, Sep. 1999, pp. 815-824.

* cited by examiner

DEVICE AND METHOD FOR DETERMINING A VOLUME OF PROJECTION OF A DUAL-AXIS COMPUTED TOMOGRAPHY SYSTEM

CROSS-REFERENCE TO PRIOR APPLICATIONS

This application is the U.S. National Phase application under 35 U.S.C. § 371 of International Application No.PCT/EP2018/075131, filed on Sep. 18, 2018 which claims the benefit of European Patent Application No. 17193169.4, filed on Sep. 26, 2017, filed on. These applications are hereby incorporated by reference herein.

FIELD OF THE INVENTION

The present invention relates to a device and a method for determining a volume of projection of a dual-axis computed tomography system with at least one shutter.

BACKGROUND OF THE INVENTION

Modern angiography systems have the possibility to acquire computed tomography images (CT-images) next to their traditional two-dimensional (2-D) functionality. The CT-functionality is implemented by letting the X-ray source and detector rotate around an object of interest, during which a sequence of images is acquired. From these images a volume is reconstructed using a reconstruction algorithm. The volume that can be reconstructed is the intersection of all projection cones. In other words, it is the volume that is covered by all projections. This volume may be defined to be the volume of projection.

Most often a circular trajectory around the object of interest is used for the detector and the X-ray tube. However, reconstructions from this trajectory are only mathematically exact in the central plane, and suffer from artifacts outside this plane. A mathematically exact reconstruction in the entire volume of interest may only be obtained with a non-planar trajectory. Non-planar trajectories may for example be realized by a motorized C-arm system, by rotating over two axes simultaneously. This may be called dual-axis computed tomography imaging. Moreover, a C-arm system may also realize a planar trajectory.

When a dual-axis trajectory is used instead of a planar circular trajectory, the size and shape of the volume of projection is increasingly difficult to estimate in advance, particularly for cone-beam computed tomography (CBCT) systems. For creating a dual-axis trajectory, the detector and the X-ray tube are moved around a primary angle which varies over more than 180 degrees plus a fan angle. Simultaneously, the detector and the X-ray tube are moved around a secondary angle and which could for example vary between −15 and +15 degree. The primary angle is analogous to the rotation angle of a planar circular trajectory. If the axis of the primary rotation is aligned with the patient head-feet axis, it is called rotation angle. Subsequently if the axis of the secondary rotation is aligned with a left-right axis it is called angulation.

The volume of projection of a circular trajectory has a shape that closely resembles a cylinder. This means that approximately everything which may be seen in the projection image may end up in the volume of projection. The volume of projection of a dual-axis trajectory is more irregular.

SUMMARY OF THE INVENTION

There may thus be a need to provide a device or a method that provides improved insight in the volume of projection of a dual-axis trajectory acquisition.

The object of the present invention is solved by the subject-matter of the independent claims; further embodiments are incorporated in the dependent claims. It should be noted that the following described aspects of the invention also apply for the system, the method and the computer program element.

According to the present invention, a device for determining a volume of projection of a dual-axis computed tomography system with at least one shutter comprises: an interface unit; a projection module; and a position determination module; wherein the interface unit is configured to receive a volume of interest for a computed tomography image showing an object; wherein the projection module is configured to determine a volume of projection of a detector based on different simulated positions of the detector on a dual-axis trajectory around the object and based on a variable simulated position of at least one shutter; and wherein the position determination module is configured to vary the simulated position of the at least one shutter for each simulated position of the detector such that the volume of projection corresponds to the volume of interest.

Within the context of this application, a "dual-axis computed tomography system" shall be understood as an X-ray system that is configured to acquire 3D images by means of a rotational scan along a dual-axis trajectory. As is known in the art, a 3D image can be reconstructed from a sequence of 2D projection images acquired during a rotation of the system, whereby for example an X-ray detector moves along the trajectory. Such X-ray system may, for example, comprise a C-arm to which an X-ray source and detector are mounted.

The volume of projection of a dual-axis computed tomography system resembles a cylinder, but with big pieces being cut-out because of the secondary rotation movement. Such an irregular shape of the volume of projection is difficult to estimate by a user beforehand, such that the extent of what will be imaged is not exactly known. Therefore, a positioning of an object of interest, e.g. a patient, such that the region of interest is completely imaged may be very difficult. This could lead to a misdiagnosis or to repeating scans in a trial and error manner resulting in a high X-ray dose being applied.

Furthermore, the field of view of an X-ray image may be refined using shutters at the X-ray tube. For example, horizontal shutters may be applied to the top and bottom of an image, such that a smaller part of an object of interest is imaged. Applying shutters may be useful for limiting an X-ray dose to be applied. In particular, it may be useful to limit or prevent X-ray dose to organs that are very sensitive to radiation, such as the thyroid gland when acquiring a head scan. It also may improve image quality due to less X-ray scatter. Applying these shutters to a dual-axis scan, however, may have an unforeseen large effect to the volume of projection. A larger than anticipated part of an object of interest may not be imaged due to the difficult predictable volume of projection of a dual-axis trajectory.

With the invention, a user may select a volume of interest in the object of interest. That selection may for example be performed by overlaying a reconstruction cylinder or cube on a pre-determined image of the object of interest. In an example, that pre-determined image may be a fluoroscopy image. The interface unit may receive the selected volume of interest. In an exemplary embodiment, the interface unit may receive the volume of interest by direct input from the user. In another exemplary embodiment, the volume of interest receives a signal created by another device which interacts with the user. The projection module then simulates a volume of projection of the detector wherein the detector is moved along the dual-axis trajectory of a dual-axis computed tomography system. While the projection module determines the volume of projection, the position determination module may simulate different shutter positions for the dual-axis computed tomography system. The position determination module adapts those simulated shutter positions for each detector position by variation such that the determined volume of projection covers the volume of interest being received by the interface unit. The volume of projection is therefore known in advance to the actual image process and the shutter positions are varied to provide a volume of projection which covers the volume of interest being indicated by the user. The volume of projection which is rather unpredictable for a user is therefore simulated first to ensure that the volume of interest occurs in the volume of projection when it is acquired by a dual-axis computed tomography imaging system. Thus, the present invention avoids that parts of an object of interest are unintentionally not imaged in dual-axis computed tomography imaging. Furthermore, the invention provides improved insight in the volume of projection of a dual-axis trajectory acquisition.

In an example, the determined volume of projection covers the complete volume of interest.

In an example, the interface unit may comprise a display and/or an input device. The display may be used to provide a pre-determined image of the object of interest and the determined volume of projection. Furthermore, the display may show the volume of interest selected by the user. The input device may be configured to select and manipulate a volume of interest in the object of interest being depicted on the display. In a further example, the user may define a dual-axis trajectory for the detector.

In an example, the shape of the determined volume of projection is irregular.

According to an example, the device further comprises: a shutter control element; wherein the shutter control element is configured to position at least one shutter of a dual-axis computed tomography system to the determined shutter position for each detector position along a dual-axis trajectory according to the determined position of the at least one shutter.

The shutter control element therefore may adjust at least one shutter of a dual-axis computed tomography system while the detector moves along the dual-axis trajectory. For each position of the detector on the dual-axis trajectory the shutter control element may adjust the shutter according to the shutter positions determined by the position determination module of the device. The shutter control element therefore ensures that the determined shutter positions are provided during the actual image acquisition with the dual-axis computed tomography system.

According to an example, the device further comprises: a feedback module; wherein the feedback module is configured to provide a visual or textual feedback if the received volume of interest cannot be covered completely by the volume of projection with the trajectory of the detector.

The feedback module warns the user if the device may not determine a volume of projection by adjusting the simulated shutter positions which completely covers the received volume of interest. Therefore, the feedback module provides the user the possibility to provide further steps. Those further steps may for example be a repositioning of the object of interest, a change of the dual-axis trajectory, or an image acquisition with the current dual-axis trajectory wherein the volume of projection does not completely cover the volume of interest, etc. The user will not be surprised by the result of the image acquisition.

According to an example, the device further comprises: a suggestion module; and a database; wherein the database is configured to store trajectories with pre-calculated volumes of projection; wherein the suggestion module is configured to choose a different trajectory from the database if the received volume of interest cannot be covered completely by the volume of projection with the trajectory of the detector and to provide it to a user.

The suggestion module may therefore amend the pre-determined dual-axis trajectory of the detector. If the current pre-determined dual-axis trajectory does not provide a simulated volume of projection covering the complete volume of interest when adjusting the simulated shutters, the suggestion module may provide another dual-axis trajectory from a database which may provide a volume of projection covering the complete volume of interest when adjusting the shutters. Therefore, the suggestion module increases the number of volumes of projection which may be simulated for a dual-axis computed tomography system before image acquisition.

According to an example, the device further comprises: a splitting module; wherein the splitting module is configured to split the volume of interest in a first portion being covered by a determined volume of projection and a second portion being outside of the volume of projection; and wherein the splitting module is configured to provide a feedback signal for the feedback module, the feedback signal comprising image data of the first and second portion.

According to an example, the splitting module is configured to split the volume of interest only if the device cannot determine a volume of projection covering the complete volume of interest.

In an example, the volume of projection is rendered when adapting it to a varied shutter position.

In a further example, the rendering of the volume of projection is performed as volume rendering. In another example, the rendering is performed as outline rendering.

According to the present invention, also a dual-axis computed tomography system for determining a volume of projection of a dual-axis computed tomography system with at least one shutter is provided. The dual-axis computed tomography system comprises: a device according to the above description; an X-ray tube; a detector; a dual-axis support and at least one shutter; wherein the dual-axis support is configured to move the X-ray tube and detector along a dual-axis trajectory; wherein the at least one shutter is arranged on the X-ray tube; and wherein the device is configured to determine a volume of projection for the detector based on the trajectory and a position of the at least one shutter.

The dual-axis computed tomography system comprising a device according to the description above avoids that the volume of projection does not cover the volume of interest being chosen by the user before starting the imaging process. Prior to the actual image acquisition with the dual-axis computed tomography system, the device determines the shutter positions for each detector position such that the volume of projection will cover the volume of interest.

According to an example, the detector is rotatable at least 180° around a first axis of the dual-axis support and further rotatable between at least −5° to +5°, particularly at least −15° to +15°, around a second axis of the dual-axis support, wherein the first axis and the second axis are non-parallel.

According to an example, the dual-axis support comprises a C-arm, an O-arm, and/or two robot arms.

According to the present invention, a method for determining a volume of projection of a dual-axis computed tomography system with at least one shutter comprises the following steps: a) receiving a volume of interest for a computed tomography image with an interface unit; and b) determining a volume of projection of a detector with a projection module based on different simulated positions of the detector on a dual-axis trajectory around the object and based on a variable simulated position of at least one shutter; c) matching the volume of projection to the volume of interest by varying a simulated position of the at least one shutter for each simulated position of the detector on the trajectory resulting in determined shutter positioning data.

The method provides a receiving of the volume of interest or a computed tomography image. That volume of interest may be chosen by a user with an interface unit. In a further step, a projection module may determine a volume of protection of a detector. The projection module simulates different positions of the detector on a dual-axis trajectory around the object of interest. Based on those different simulated positions of the detector, the position of at least one shutter is varied to match the volume of projection of the detector to the volume of interest. This may for example be performed with a position determination module. The position determination module may adapt those shutter positions for each detector position by variation such that the volume of projection covers the volume of interest being received by the interface unit. The volume of projection is therefore known in advance to the actual imaging process and the shutter positions are varied to provide a volume of projection which covers the volume of interest being indicated by the user. The volume of projection which is rather unpredictable for a user is therefore simulated first to ensure that the volume of interest is arranged in the volume of projection when an image is acquired by a dual-axis computed tomography imaging system. Thus, the present invention avoids that parts of an object of interest are unintentionally not imaged in dual-axis computed tomography imaging.

According to an example, the method further comprises the step: d) positioning at least one shutter of a dual-axis computed tomography system according to the determined shutter positioning data while positioning a detector of the dual-axis computed tomography system along the trajectory.

That step may provide control signals for shutters of a dual-axis computed tomography system. The determined shutter positions of step c) may be provided to the dual-axis computed tomography system such that the shutters may be positioned for each detector position on the dual-axis trajectory within the image acquisition.

In an example, step b) is performed before step a); and wherein the method further comprises the step: fitting a volume of interest into the determined volume of projection.

In an example, the method further comprises the step: re-determining the volume of projection if the position of the shutter is changed.

According to the present invention, a computer program element for controlling an apparatus according to the description mentioned above, which, when being executed by a processing unit, is adapted to perform the method steps being described above.

According to the present invention, a computer readable medium having stored the computer program element mentioned above.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
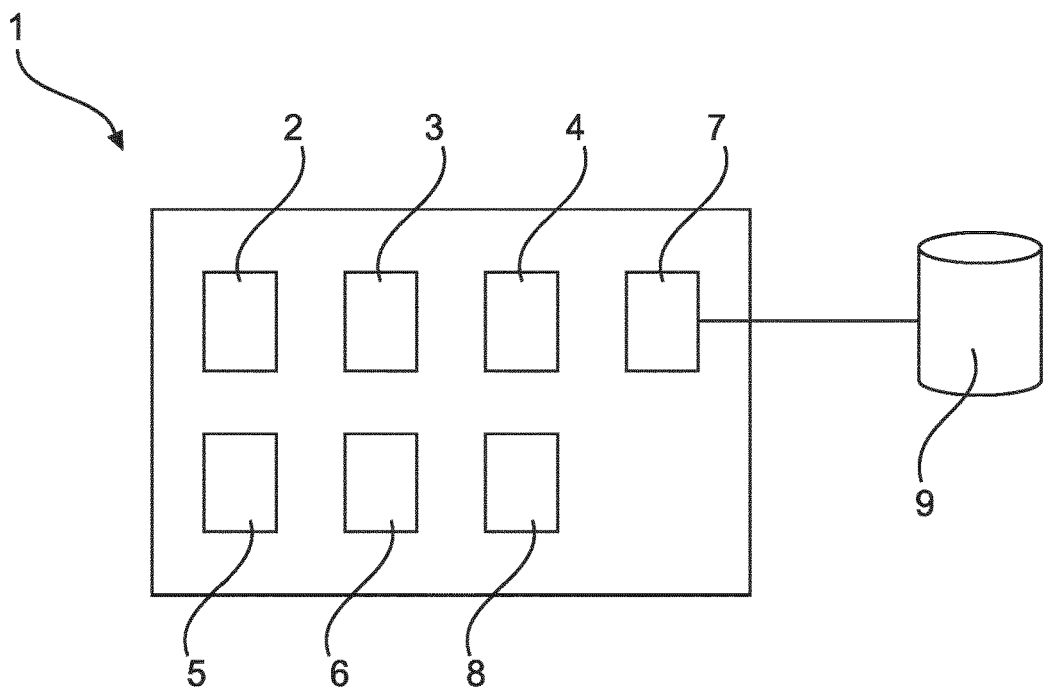
FIG. 1 shows a schematic view of the device for determining a volume of projection for a detector of a dual-axis computed tomography system with at least one shutter.

FIG. 1 shows a device for determining a volume of projection for a detector of a dual-axis computed tomography system with at least one shutter. The device is referenced with reference number 1.

The device 1 comprises an interface unit 2, a projection module 3, a position determination module 4, a shutter control element 5, a feedback module 6, a suggestion module 7, and a splitting module 8.

The interface module 2 may receive a volume of interest 44 for a computed tomography image showing an object 22. The volume of interest 44 may be chosen by a user by marking a region in a previously acquired image of the object of interest 22. The chosen region may be received by the interface module 2 and may be called the volume of interest 44. The volume of interest 44 may be the whole object of interest 22 or a part of the object of interest 22.

Furthermore, in an exemplary embodiment, the interface module 2 may receive the volume of interest 44 directly from the user by direct input. This means that the user directly interacts with the interface module 2 for providing the volume of interest 44.

In another exemplary embodiment, the interface module 2 may receive the volume of interest 44 by a further element, e.g. by a computer. The user may interact with the computer for indicating the volume of interest 44. The computer may then transmit the volume of interest 44 to the interface module 2.

The projection module 3 simulates a volume of projection 41, 42, 46 by simulating an X-ray tube 14 and a correspondingly arranged detector 16 which move along a dual-axis trajectory around the object of interest 22. The detector 16 and the X-ray tube 14 are arranged on opposite sides of the object of interest 22, wherein the X-ray tube 14 emits X-ray radiation which translates from the X-ray tube 14 to the detector 16 passing the object of interest 22. The projection module 3 then simulates a projection cone for each position of the detector 16. The intersection of all projection cones along the dual-axis trajectory determines the volume of projection. The projection module 3 may consider at least one shutter 15 at the X-ray tube 14 during the determination of the volume of projection 41, 42, 46.

The position of the shutter 15 at the X-ray tube 14 delimits the field of view of the detector 16. Therefore, at a certain position on the dual-axis trajectory a shutter 15 may block the view on certain portions of the object of interest 22. If the view on certain aspects of the object of interest 22 is blocked at some positions of the detector 16 along the trajectory it may not be possible to provide a computed tomography image of those regions.

Therefore, during the determination of the volume of projection 41, 42, 46, the position determination module 4 varies a position of the shutter 15 for each position of the detector 16 on the dual-axis trajectory such that the shutter 15 does not block the view of the detector 16 on the volume of interest 44. For that, the position determining module 4 may check several positions for the shutter 15 and a certain position of the detector 16. For each of shutter positions the projection cone of the detector 16 is determined. The position determining module 4 may select a position for the shutter 15 which allows the detector 16 to receive a projection cone comprising the volume of interest 44, wherein the shutter 15 still may provide a reduction of the X-ray scattering and X-ray absorption to organs outside the volume of interest 44.

A splitting module 8 may assess whether the determined volume of projection 41, 42, 46 corresponds to the volume of interest 44. The splitting module 8 splits the volume of interest 44 in the first portion which is covered by the determined volume of projection 41, 42, 46 and a second portion which is not covered by the determined volume of projection 41, 42, 46. This means, that the splitting module 8 determines a portion of the volume of interest 44 which is arranged outside of the volume of projection 41, 42, 46.

The splitting module 8 may only then split the volume of interest 44 if no volume of projection 41, 42, 46, may be determined which covers the volume of interest 44. This means, if the volume of projection 41, 42, 46 covers the complete volume of interest 44 the splitting module 8 will not determine a split of the volume of interest 44.

The splitting module 8 may further provide a feedback signal comprising image data of the first and second portion. The feedback signal may be received by a feedback module 6 and/or a suggestion module 7.

The suggestion module 7 may retrieve a further dual-axis trajectory for the detector 16 from a database 9, wherein the database stores trajectories with pre-determined volumes of projection. The suggestion module 7 may choose one of those trajectories to replace the actual dual-axis trajectory for the detector 16. The suggestion module 7 will only replace the actual dual-axis trajectory for the detector 16 if the position determination module 4 is not able to determine any shutter position such that the volume of projection 41, 42, 46 may cover the complete volume of interest 44, i.e. if even fully opened shutters 15 will not result in a volume of projection 41, 42, 46 which corresponds to the volume of interest 44. Therefore, the suggestion module 7 introduces a further level of varying the image acquisition conditions with the dual-axis computed tomography system 10 by changing the use of dual-axis trajectory for the acquisition of the image.

If for a certain position of a detector 16, the position of the at least one shutter 15 may not be adapted such that the volume of projection 41, 42, 46 may cover the volume of interest 44, the feedback module 6 may provide a visual or textual feedback for the user. The feedback may be provided on a display (not shown). Therefore, the user knows that with the actual positioning of the object of interest 22 and with the actual dual-axis trajectory the volume of projection 41, 42, 46 may not cover the volume of interest 44.

Figure 2:
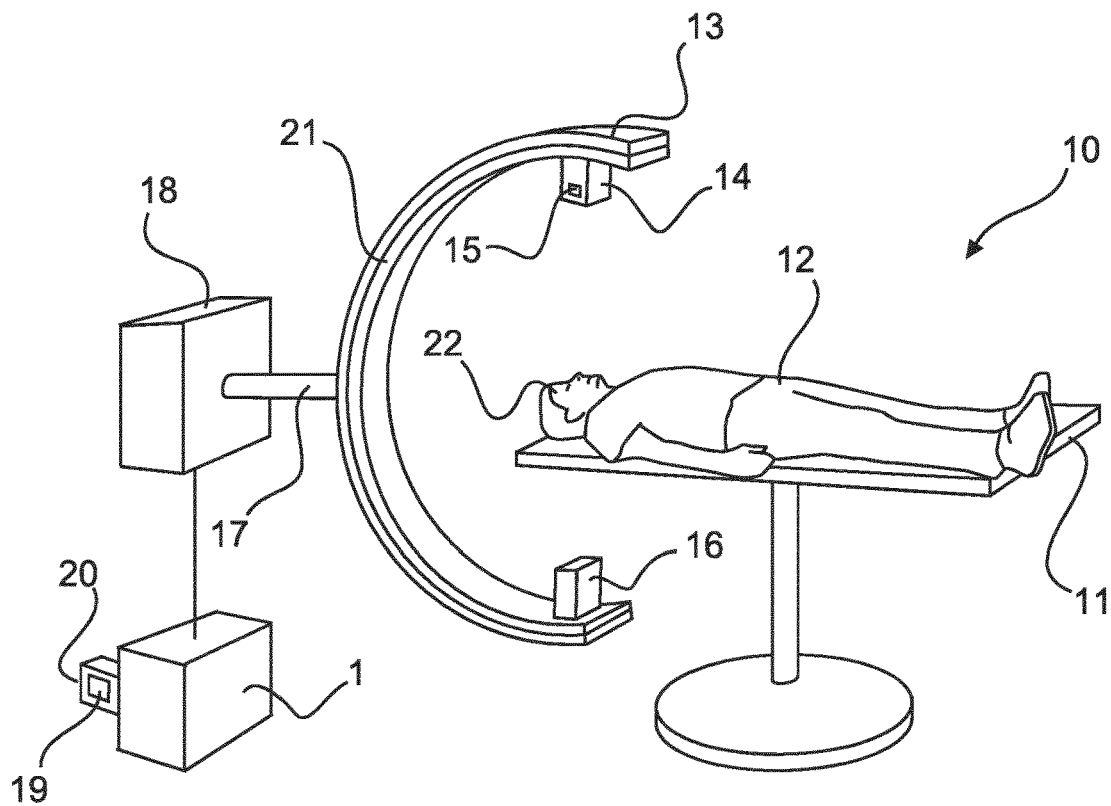
FIG. 2 shows a schematic view of the system for determining a volume of projection for a detector of a dual-axis computed tomography system with at least one shutter.

FIG. 2 shows a dual-axis computed tomography system with at least one shutter. The dual-axis computed tomography system is referenced with reference number 10.

The dual-axis computed tomography system 10 comprises an X-ray tube 14, a detector 16, a dual-axis support 13, and at least one shutter 15, the at least one shutter 15 being arranged on the X-ray tube 14.

It is preferred that the X-ray tube 14 comprises at least two shutters 15. The shutters 15 may be arranged within the X-ray tube 14. Depending on their position, the fields of view of the detector 16 on different positions of a trajectory may be adjusted.

In FIG. 2, the dual-axis support 13 is formed as a C-arm. The X-ray tube 14 and the detector 16 are arranged on opposite arms of the C-arm. X-ray radiation leaving the X-ray tube 14 will translate through the object of interest 22, here being the head of a patient 12 being laid down on a patient support element 11. Then, after passing the object of interest 22 the X-ray radiation will be detected by the detector 16.

A rotatable bearing axis 17 bears the dual-axis support 13. The dual-axis support 13 may rotate the detector 16 and the X-ray tube 14 around at least 180° around the object 22. Furthermore, a bearing element 18 bears the axis 17 such that the dual-axis support 13 may be attached to a wall or a further element.

The dual-axis support comprises a sliding element 21 which may slide along the dual-axis support. In FIG. 2 the sliding element 21 has a C-shape like the shown C-arm. The detector 16 and the X-ray tube 14 are attached to the sliding element. Thus, the detector 16 and the X-ray tube 14 may be pivoted around a second axis, the second axis and the axis 17 being not parallel. The rotation around the second axis may be at least between −5° to +5°, particularly at least between −15° to +15°.

Figure 3A:
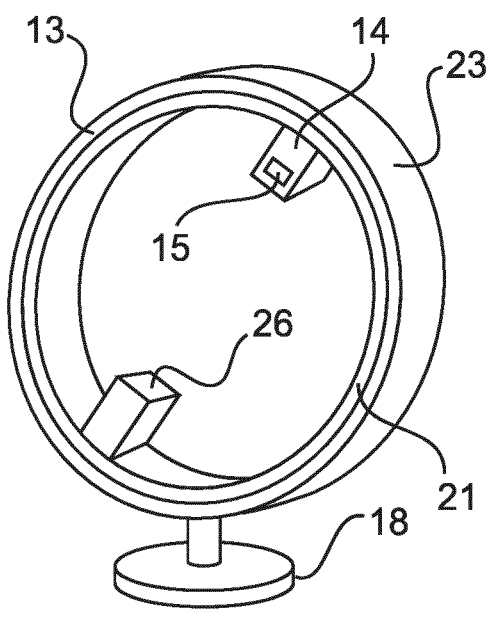
FIG. 3a, b show schematic views of embodiments of the dual-axis support.

FIG. 3a shows another embodiment of the dual-axis support 13. The dual-axis support 13 may be formed as an O-arm 23.

Figure 3B:
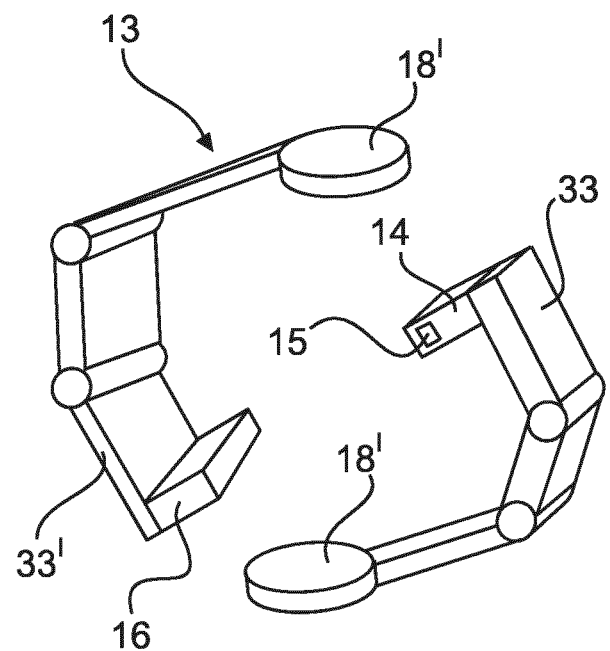

In a further embodiment being shown in FIG. 3b, the dual-axis support 13 is formed out as two robot arms 33, 33'. The X-ray tube 14 is arranged on one arm 33. The detector 16 is arranged on the other arm 33'. Both robot arms 33, 33' are connected to a rotatable bearing 18'. That bearing 18' allows a rotation around at least 180°. The robot arms 33, 33' perform a rotation around a second-axis movement while the X-ray tube 14 and the detector 16 are turned around an object of interest by the rotatable bearings 18'. During the actual image acquisition with the dual-axis computed tomography system 10, the shutter control element 5 controls the at least one shutter 15 of the dual-axis computed tomography system 10 according to the shutter positions being determined by the position determination module 4. Due to the control of the shutter control element 5 the dual-axis computed tomography system 10 may position the shutter 15 according to the determined shutter positions.

This means, that for each position of the detector 16 on the dual-axis trajectory being provided by the dual-axis computed tomography system 10, the shutter control element 5 aligns a pre-determined position for the shutter 15.

Figure 6:
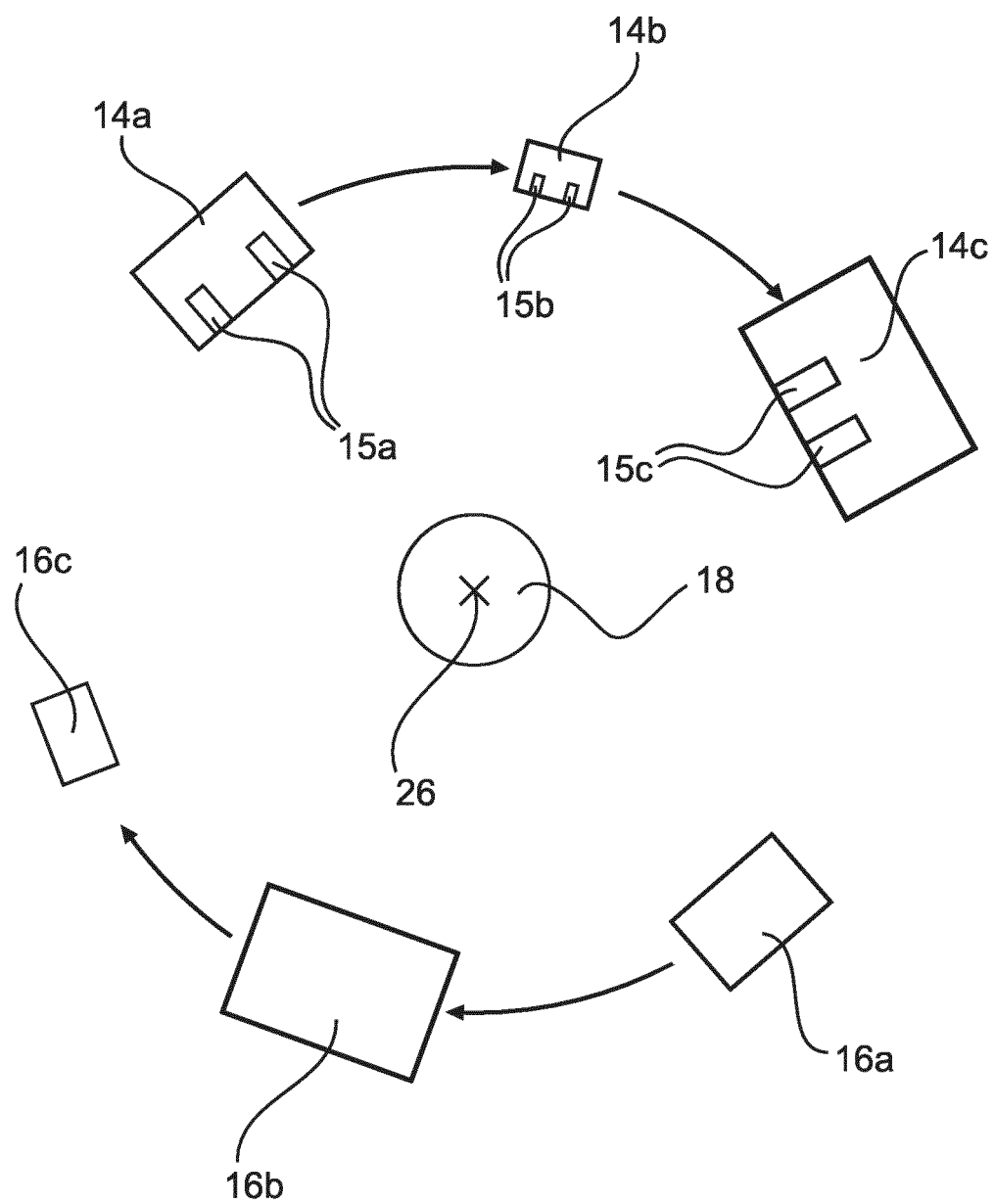
FIG. 6 shows a schematic view of different positions of a detector and X-ray tube along a dual-axis trajectory.

An example of a position of a detector 16 along a dual-axis trajectory is shown in FIG. 6, wherein the positions of two shutters 15 are varied for each position of the detector 16. FIG. 6 shows three positions of the detector 16, the positions being denoted with a, b, and c. For each position the reference numbers of the detector 16, the X-ray tube 14, and the shutters 15 are indexed with a, b, and c.

In the first position, the detector 16a is in a starting position. Furthermore, the X-ray tube 14a also is in a starting position, wherein the shutters 15a are in a certain first position. In the second position, the detector 16b and the X-ray tube 14b have been rotated around a primary axis 26 and further be rolled around a secondary axis which is orthogonal to the primary axis 26. Therefore, the detector 16b is closer to the viewer of FIG. 6 than in the first position. Furthermore, the X-ray tube 14b is farer away from the viewer of FIG. 6 than in the first position. Furthermore, the shutters 15b have another position than in the first position. In the third position, the detector 16c and the X-ray tube 14c a further rotated around the primary axis 26. Further, the detector 16c and the X-ray tube 14c are rolled around the secondary axis but in the opposite direction as in the second position. Thus, the detector 16c is farer away from the viewer than in the second position. Furthermore, the X-ray tube 14c is closer to the viewer than in the second position. The shutters 15c are now closer to each other than in the first and the second position.

This shows, that for each detector position a specific shutter position is adjusted according to the shutter positions being determined by the device 1.

Figure 5A:
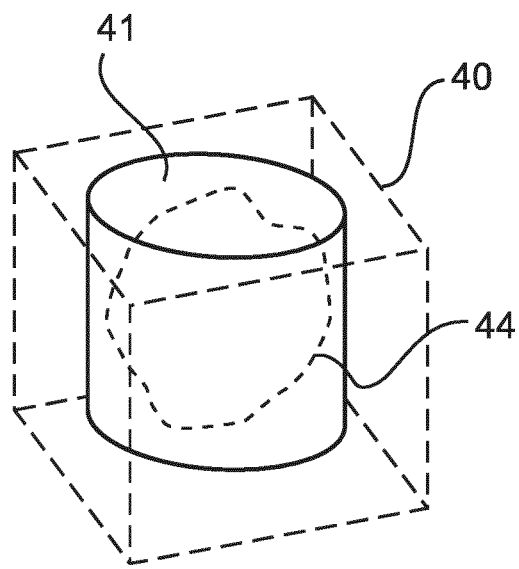
FIG. 5a, b, c show schematic views of volumes of projections and volumes of interest.

FIG. 5 a shows a volume 40 in which a user may choose a volume of interest and in which a volume of projection may be depicted. The volume of interest 44 is in the volume 40. Furthermore, FIG. 5a shows a volume of projection 41 which is determined from a planar trajectory without a rotation around a second-axis movement.

Figure 5B:
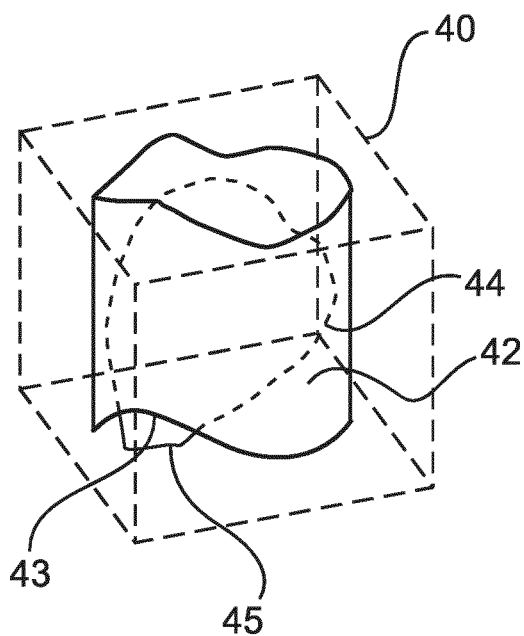

FIG. 5b shows a simulated volume of projection 42 which is determined with a detector 16 being moved on a dual-axis trajectory. The shape of the volume of projection 42 is irregular. That shape cannot be predicted by a user. Can be seen that a portion 45 of the object of interest 44 is not covered by the volume of projection 42 since at that position 43, the field of view of the detector 16 may be blocked by a shutter 15.

Figure 5C:
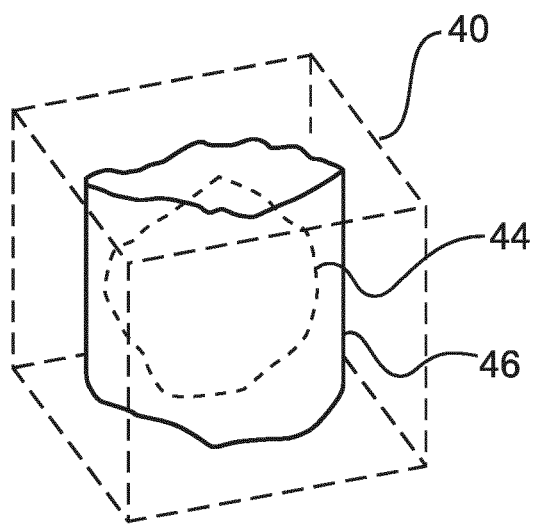

In FIG. 5c, a volume of projection 46 is shown which is determined with varied shutter positions during a movement of a detector 16 along a dual-axis trajectory. The volume of projection 46 now covers the volume of interest 44. At the position corresponding to the position 43 in FIG. 5b, the volume of projection is now such that it covers the portion 45 of the object of interest 44 which has not been covered in FIG. 5b.

Figure 4:
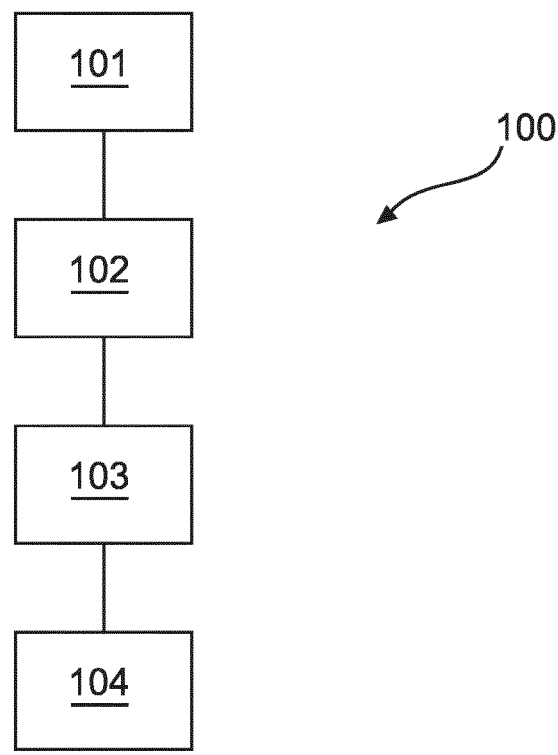
FIG. 4 shows a schematic flow chart of the method for determining a volume of projection for a detector of a dual-axis computed tomography system with at least one shutter.

FIG. 4 shows a schematic flow chart for the method 100 for determining a volume of projection for a detector of a dual-axis computed tomography system with at least one shutter.

In step a), a volume of interest 44 for a computed tomography image is received 101 with an interface unit. The interface module 2 may receive a volume of interest 44 for a computed tomography image showing an object 22. The volume of interest 44 may be chosen by a user by marking a region in a previously acquired image of the object of interest 22. The chosen region may be received by the interface module 2 and may be called the volume of interest 44. The volume of interest 44 may be the whole object of interest 22 or a part of the object of interest 22.

Furthermore, in an exemplary embodiment, the interface module 2 may receive the volume of interest 44 directly from the user by direct input. This means that the user directly interacts with the interface module 2 for providing the volume of interest 44.

In another exemplary embodiment, the interface module 2 may receive the volume of interest 44 by a further element, e.g. by a computer. The user may interact with the computer for indicating the volume of interest 44. The computer may then transmit the volume of interest 44 to the interface module 2.

In a further step b), a volume of projection 41, 42, 46 of a detector with a projection module based on different simulated positions of the detector on a trajectory around the object may be determined 102. The determining 102 may be based on a variable simulated position of at least one shutter. Furthermore, the trajectory may be defined by a dual-axis computed tomography system. The projection module 3 simulates a volume of projection 41, 42, 46 by simulating an X-ray tube 14 and a correspondingly arranged detector 16 which move along a dual-axis trajectory around the object of interest 22. The detector 16 and the X-ray tube 14 are arranged on opposite sides of the object of interest 22, wherein the X-ray tube 14 emits X-ray radiation which translates from the X-ray tube 14 to the detector 16 passing the object of interest 22. The projection module 3 then simulates a projection cone for each position of the detector 16. The intersection of all projection cones along the dual-axis trajectory determines the volume of projection. The projection module 3 may consider at least one shutter 15 at the X-ray tube 14 during the determination of the volume of projection 41, 42, 46.

The position of the shutter 15 at the X-ray tube 14 delimits the field of view of the detector 16. Therefore, at a certain position on the dual-axis trajectory a shutter 15 may block the view on certain portions of the object of interest 22. If the view on certain aspects of the object of interest 22 is blocked at some positions of the detector 16 along the trajectory it may not be possible to provide a computed tomography image of those regions.

In step c), the volume of projection 41, 42, 46 is matched 103 to the volume of interest 44 by varying a simulated position of the at least one shutter of each simulated position of the detector on the trajectory. The result is a determined shutter positioning data.

Therefore, during the determination of the volume of projection 41, 42, 46, the position determination module 4 varies a position of the shutter 15 for each position of the detector 16 on the dual-axis trajectory such that the shutter 15 does not block the view of the detector 16 on the volume of interest 44. For that, the position determining module 4 may check several positions for the shutter 15 and a certain position of the detector 16. For each of shutter positions the projection cone of the detector 16 is determined. The position determining module 4 may select a position for the shutter 15 which allows the detector 16 to receive a projection cone comprising the volume of interest 44, wherein the shutter 15 still may provide a reduction of the X-ray scattering and X-ray absorption to organs outside the volume of interest 44.

A splitting module 8 may assess whether the determined volume of projection 41, 42, 46 corresponds to the volume of interest 44. The splitting module 8 splits the volume of interest 44 in the first portion which is covered by the determined volume of projection 41, 42, 46 and a second portion which is not covered by the determined volume of projection 41, 42, 46. This means, that the splitting module 8 determines a portion of the volume of interest 44 which is arranged outside of the volume of projection 41, 42, 46.

The splitting module 8 may only then split the volume of interest 44 if no volume of projection 41, 42, 46, may be determined which covers the volume of interest 44. This means, if the volume of projection 41, 42, 46 covers the complete volume of interest 44 the splitting module 8 will not determine a split of the volume of interest 44.

The splitting module 8 may further provide a feedback signal comprising image data of the first and second portion. The feedback signal may be received by a feedback module 6 and/or a suggestion module 7.

The suggestion module 7 may retrieve a further dual-axis trajectory for the detector 16 from a database 9, wherein the database stores trajectories with pre-determined volumes of projection. The suggestion module 7 may choose one of those trajectories to replace the actual dual-axis trajectory for the detector 16. The suggestion module 7 will only replace the actual dual-axis trajectory for the detector 16 if the position determination module 4 is not able to determine any shutter position such that the volume of projection 41, 42, 46 may cover the complete volume of interest 44, i.e. if even fully opened shutters 15 will not result in a volume of projection 41, 42, 46 which corresponds to the volume of interest 44. Therefore, the suggestion module 7 introduces a further level of varying the image acquisition conditions with the dual-axis computed tomography system 10 by changing the use of dual-axis trajectory for the acquisition of the image.

If for a certain position of a detector 16, the position of the at least one shutter 15 may not be adapted such that the volume of projection 41, 42, 46 may cover the volume of interest 44, the feedback module 6 may provide a visual or textual feedback for the user. The feedback may be provided on a display (not shown). Therefore, the user knows that with the actual positioning of the object of interest 22 and with the actual dual-axis trajectory the volume of projection 41, 42, 46 may not cover the volume of interest 44.

It is preferred that the X-ray tube 14 comprises at least two shutters 15. The shutters 15 may be arranged within the X-ray tube 14. Depending on their position, the fields of view of the detector 16 on different positions of a trajectory may be adjusted.

In FIG. 2, the dual-axis support 13 is formed as a C-arm. The X-ray tube 14 and the detector 16 are arranged on opposite arms of the C-arm. X-ray radiation leaving the X-ray tube 14 will translate through the object of interest 22, here being the head of a patient 12 being laid down on a patient support element 11. Then, after passing the object of interest 22 the X-ray radiation will be detected by the detector 16.

A rotatable bearing axis 17 bears the dual-axis support 13. The dual-axis support 13 may rotate the detector 16 and the X-ray tube 14 around at least 180° around the object 22.

Furthermore, a bearing element 18 bears the axis 17 such that the dual-axis support 13 may be attached to a wall or a further element.

The dual-axis support comprises a sliding element 21 which may slide along the dual-axis support. In FIG. 2 the sliding element 21 has a C-shape like the shown C-arm. The detector 16 and the X-ray tube 14 are attached to the sliding element. Thus, the detector 16 and the X-ray tube 14 may be pivoted around a second axis, the second axis and the axis 17 being not parallel. The rotation around the second axis may be at least between −5° to +5°, particularly at least between −15° to +15°.

FIG. 3a shows another embodiment of the dual-axis support 13. The dual-axis support 13 may be formed as an O-arm 23.

In a further embodiment being shown in FIG. 3b, the dual-axis support 13 is formed out as two robot arms 33, 33'. The X-ray tube 14 is arranged on one arm 33. The detector 16 is arranged on the other arm 33'. Both robot arms 33, 33' are connected to a rotatable bearing 18'. That bearing 18' allows a rotation around at least 180°. The robot arms 33, 33' perform a rotation around a second-axis movement while the X-ray tube 14 and the detector 16 are turned around an object of interest by the rotatable bearings 18'.

In a further step d) of the method, the at least one shutter may be positioned 104 according to the determined shutter positioning data while positioning the detector of the dual-axis computed tomography system along the trajectory. During the actual image acquisition with the dual-axis computed tomography system 10, the shutter control element 5 controls the at least one shutter 15 of the dual-axis computed tomography system 10 according to the shutter positions being determined by the position determination module 4. Due to the control of the shutter control element 5 the dual-axis computed tomography system 10 may position the shutter 15 according to the determined shutter positions.

This means, that for each position of the detector 16 on the dual-axis trajectory being provided by the dual-axis computed tomography system 10, the shutter control element 5 aligns a pre-determined position for the shutter 15.

An example of a position of a detector 16 along a dual-axis trajectory is shown in FIG. 6, wherein the positions of two shutters 15 are varied for each position of the detector 16. FIG. 6 shows three positions of the detector 16, the positions being denoted with a, b, and c. For each position the reference numbers of the detector 16, the X-ray tube 14, and the shutters 15 are indexed with a, b, and c.

In the first position, the detector 16a is in a starting position. Furthermore, the X-ray tube 14a also is in a starting position, wherein the shutters 15a are in a certain first position. In the second position, the detector 16b and the X-ray tube 14b have been rotated around a primary axis 26 and further be rolled around a secondary axis which is orthogonal to the primary axis 26. Therefore, the detector 16b is closer to the viewer of FIG. 6 than in the first position. Furthermore, the X-ray tube 14b is farer away from the viewer of FIG. 6 than in the first position. Furthermore, the shutters 15b have another position than in the first position. In the third position, the detector 16c and the X-ray tube 14c a further rotated around the primary axis 26. Further, the detector 16c and the X-ray tube 14c are rolled around the secondary axis but in the opposite direction as in the second position. Thus, the detector 16c is farer away from the viewer than in the second position. Furthermore, the X-ray tube 14c is closer to the viewer than in the second position. The shutters 15c are now closer to each other than in the first and the second position.

This shows, that for each detector position a specific shutter position is adjusted according to the shutter positions being determined by the device 1.

In a further exemplary embodiment of the inventive method, step b) may be performed before step a). This means, that first the volume of projection 41, 42, 46 may be calculated from the dual-axis trajectory of the detector. Then based on the volume of projection 41, 42, 46 which has been calculated, a user may choose a volume of interest 44. That volume of interest 44 may be provided to the method by the interface module. This has the advantage that a user may position the volume of interest 44 precisely inside the volume of projection. If the acquisition protocol is changed, i.e. if the shutter position is changed, the volume of projection 41, 42, 46 may be rendered again.

The volume of projection 41, 42, 46 may be overlaid on a fluoroscopy image with shutters applied. Based on this overlay, a user may choose the volume of interest 44, wherein the user may precisely adapted volume of interest 44 to the volume of projection.

In another exemplary embodiment of the present invention, a computer program or a computer program element 19 is provided, that is characterized by being adapted to execute the method steps of the method 100 according to one of the preceding embodiments, on an appropriate system.

The computer program element 19 might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element 19 might be able to provide all necessary steps to fulfil the procedure of an exemplary embodiment of the method as described above.

According to a further exemplary embodiment of the present invention, a computer readable medium 20, such as a CD-ROM, is presented wherein the computer readable medium 20 has a computer program element 19 stored on it which computer program element 19 is described by the preceding section. A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated, and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A device for determining a volume of projection of a dual-axis computed tomography system with at least one shutter, the device comprising:
   an interface unit configured to receive a volume of interest for a computed tomography image showing an object;
   a projection module configured to determine a volume of projection of a detector based on different simulated positions of the detector on a dual-axis trajectory around the object and based on a variable simulated position of at least one shutter; and
   a position determination module configured to vary the variable simulated position of the at least one shutter for at least one of the different simulated positions of the detector such that the volume of projection corresponds to the volume of interest.

2. The device according to claim 1, further comprising:
   a shutter control element configured to position the at least one shutter to a shutter position determined by the position determination module for each detector position along the dual-axis trajectory.

3. The device according to claim 1, further comprising:
   a feedback module configured to provide a visual or textual feedback if the received volume of interest cannot be covered completely by the volume of projection with the dual-axis trajectory of the detector.

4. The device according to claim 1, further comprising:
   a database configured to store trajectories with pre-determined volumes of projection; and
   a suggestion module configured to choose a different trajectory from the database if the received volume of interest cannot be covered completely by the volume of projection with the dual-axis trajectory of the detector and to provide the different trajectory to a user.

5. The device according to claim 1, further comprising:
   a splitting module configured to split the volume of interest in a first portion being covered by the volume of projection and a second portion being outside of the volume of projection; and
   wherein the splitting module is configured to provide a feedback signal, the feedback signal comprising image data of the first and second portion.

6. The device according to claim 5, wherein the splitting module is configured to split the volume of interest only if the device cannot determine the volume of projection to cover the complete volume of interest.

7. A dual-axis computed tomography system for determining a volume of projection, the dual-axis computed tomography system comprising:
   a dual-axis support configured to move an X-ray tube and a detector along a dual-axis trajectory;
   at least one shutter arranged on the X-ray tube; and a device configured to determine a volume of projection for the detector based on the dual-axis trajectory and a position of the at least one shutter, the device comprising:

an interface unit configured to receive a volume of interest for a computed tomography image showing an object, a projection module configured to determine the volume of projection for the detector based on different simulated positions of the detector on the dual-axis trajectory around the object and based on a variable simulated position of the at least one shutter, and a position determination module configured to vary the variable simulated position of the at least one shutter for at least one of the different simulated positions of the detector such that the volume of projection corresponds to the volume of interest.

8. The system according to claim 7, wherein the detector is rotatable at least 180° around a first axis of the dual-axis support and further rotatable between at least −5° to +5°, particularly at least −15° to +15°, around a second axis of the dual-axis support, wherein the first axis and the second axis are non-parallel.

9. The system according to claim 7, wherein the dual-axis support comprises a C-arm, an O-arm, and/or two robot arms.

10. The system according to claim 7, wherein the device further comprises:
a shutter control element configured to position the at least one shutter to a shutter position determined by the position determination module for each detector position along the dual-axis trajectory.

11. The system according to claim 7, wherein the device further comprises:
a feedback module is configured to provide a visual or textual feedback if the received volume of interest cannot be covered completely by the volume of projection with the dual-axis trajectory of the detector.

12. The system according to claim 7, wherein the device further comprises:
a database configured to store trajectories with pre-determined volumes of projection; and
a suggestion module configured to choose a different trajectory from the database if the received volume of interest cannot be covered completely by the volume of projection with the dual-axis trajectory of the detector and to provide it the different trajectory to a user.

13. The system according to claim 7, wherein the device further comprises:
a splitting module configured to split the volume of interest in a first portion being covered by the volume of projection and a second portion being outside of the volume of projection; and
wherein the splitting module is configured to provide a feedback signal comprising image data of the first and second portion.

14. The system according to claim 13, wherein the splitting module is configured to split the volume of interest only if the device cannot determine the volume of projection to cover the complete volume of interest.

15. A method for determining a volume of projection of a dual-axis computed tomography system with at least one shutter, the method comprising:
receiving a volume of interest for a computed tomography image by an interface unit;
determining a volume of projection of a detector, by a projection module, based on different simulated positions of the detector on a dual-axis trajectory around an object and based on a variable simulated position of at least one shutter; and
matching the volume of projection to the volume of interest by varying the variable simulated position of the at least one shutter for each of the different simulated positions of the detector on the dual-axis trajectory resulting in determined shutter positioning data.

16. The method according to claim 15, further comprising:
positioning the at least one shutter according to the determined shutter positioning data while positioning the detector along the dual-axis trajectory.

17. The method according to claim 15, further comprising:
providing a visual or textual feedback if the received volume of interest cannot be covered completely by the volume of projection with the dual-axis trajectory of the detector.

18. The method according to claim 15, further comprising:
storing, in a database, trajectories with pre-determined volumes of projection; and
choosing a different trajectory from the database if the received volume of interest cannot be covered completely by the volume of projection with the dual-axis trajectory of the detector and to provide the different trajectory to a user.

19. The method according to claim 15, further comprising:
splitting the volume of interest in a first portion being covered by the volume of projection and a second portion being outside of the volume of projection; and
providing a feedback signal comprising image data of the first and second portion.

20. A non-transitory computer-readable storage medium having stored a computer program comprising instructions for controlling a device for determining a volume of projection of a dual-axis computed tomography system with at least one shutter, the instructions, when the computer program is executed by a computer, cause the computer to:
receive a volume of interest for a computed tomography image by an interface unit;
determine a volume of projection of a detector, by a projection module, based on different simulated positions of the detector on a dual-axis trajectory around an object and based on a variable simulated position of at least one shutter; and
match the volume of projection to the volume of interest by varying the variable simulated position of the at least one shutter for each of the different simulated positions of the detector on the dual-axis trajectory resulting in determined shutter positioning data.

* * * * *